United States Patent
Wedekamp

(10) Patent No.: US 6,193,938 B1
(45) Date of Patent: Feb. 27, 2001

(54) DEVICE FOR TREATING LIQUIDS WITH UV-RADIATION

(75) Inventor: Horst Wedekamp, Herford (DE)

(73) Assignee: Wedeco AG Water Technology, Duesseldorf (DE)

( * ) Notice: Subject to any disclaimer, the term of this patent is extended or adjusted under 35 U.S.C. 154(b) by 0 days.

(21) Appl. No.: 09/271,090

(22) Filed: Mar. 17, 1999

(51) Int. Cl.[7] .................... B01J 19/12; C02F 1/48; E02B 7/08
(52) U.S. Cl. .................... 422/186.3; 210/748; 405/113
(58) Field of Search .................... 422/186.3; 204/275.1; 405/113; 210/748

(56) References Cited

U.S. PATENT DOCUMENTS

| | | | |
|---|---|---|---|
| 3,595,786 | * | 7/1971 | Horvath et al. .................... 210/198.1 |
| 3,967,453 | * | 7/1976 | Bauzil .................... 405/115 |
| 4,816,145 | * | 3/1989 | Goudy, Jr. .................... 422/186.3 |
| 5,049,252 | * | 9/1991 | Murrell .................... 204/268 |
| 5,200,156 | * | 4/1993 | Wedekamp .................... 422/186.3 |
| 5,616,245 | * | 4/1997 | Albrecht .................... 210/371 |
| 5,780,860 | * | 7/1998 | Gadgil et al. .................... 250/432 R |
| 5,888,388 | * | 3/1999 | Kirk .................... 210/170 |

* cited by examiner

Primary Examiner—Kathryn Gorgos
Assistant Examiner—Thao Tran
(74) Attorney, Agent, or Firm—Collard & Roe, P.C.

(57) ABSTRACT

A device for treating waste water with UV-radiation is in the form of an upwardly open channel with a bottom surface and two vertical side walls, which includes a UV-irradiation chamber and a downstream outlet chamber adjoining the UV chamber. UV-radiation sources are installed in the irradiation chamber. A damming wall terminating the outlet chamber is in the form of an extension of the channel bottom raised upwardly in a slanted way at a flat angle to the direction of flow. A multitude of tubes extending perpendicular to the direction of flow of the waste water are present on the slanted damming wall. These tubes are open at both ends. The top ends of the tubes form overflow edges for the waste water. The damming wall has openings in the locations where the tubes are secured on the damming wall. These openings correspond to the cross sections of the tubes, so that the waste water flowing across the overflow edges of the tubes can drain off through the openings.

14 Claims, 3 Drawing Sheets

DEVICE FOR TREATING LIQUIDS WITH UV-RADIATION

BACKGROUND OF THE INVENTION

1. Field of the Invention

The present invention relates to a device for treating liquids with UV-radiation.

2. The Prior Art

These devices are preferably used in sewage purification (or treatment) plants. Before the purified (or prepurified) waste water effluent from the sewage treatment plant is discharged into natural waters, it always has to be disinfected a number of times. The waste water purified in the treatment plant is for this purpose subjected to a treatment with ultraviolet radiation (UV-radiation).

The devices provided for such treatment have an irradiation chamber through which the waste water flows. The irradiation chamber is equipped with UV radiation sources. These sources are formed by UV radiation lamps, which are enclosed in protective tubes made from quartz for protecting the lamps against the waste water. These protective tubes are permeable to the UV-rays which, therefore, can penetrate the waste water.

In addition to the irradiation chamber, the known devices comprise an outlet chamber arranged downstream of the irradiation chamber. The waste water exposed to the UV-radiation is received in the outlet chamber; and the now-purified, disinfected waste water can be discharged from there into the discharge system.

EP 0 687 201 B1 discloses a purification device with an irradiation chamber designed in the form of a completely closed chamber shaped like a tube. The waste water is forced through the irradiation chamber under pressure, which leads to an increased flow rate of the waste water in the irradiation chamber.

In such devices, the outlet chamber adjoining the irradiation chamber in the downstream direction has installed elements in the form of terminating walls serving as weir elements. The terminating walls are designed, for example, in the form of shutoff flaps (or shutters), overflow weirs or motor weirs extending vertically relative to the direction of flow of the flowing waste water. The water dams up in front of the installed elements. The water then flows off over the so-called overflow edges into the discharge system. Thus the water flows over the upper edges or below the shutoff flaps or shutters, and is then admitted into the natural waters.

In the known devices, the installed elements of the outlet chamber serving as weir elements comprise a plurality of rectangular or also triangular individual chambers with vertical termination walls serving as damming walls. These elements are installed next to each other. This increases the overall length of the overflow edge for the waste water. Therefore, even relatively large quantities of waste water can flow off over the overflow edge and then be discharged into the drain system without substantially raising the water level.

Since the known devices require a great overall length for the available overflow edge in order to avoid high variations in the water level, the dimensions of the chambers are very large when viewed in the direction of flow of the waste water. Thus the complete device requires a great deal of overall space. This, furthermore, leads to increased expenditures with respect to manufacturing and operating costs.

Another drawback is that the waste water received in the outlet chamber from the irradiation chamber impacts quasi-vertical termination walls of the elements installed in the outlet chamber. This impact will slow down the water contacting these walls. This causes the water to back up, and such backwater may extend back into the irradiation chamber upstream. This will lead to uneven flow of the waste water. Such nonuniform flow, however, is disadvantageous for treating waste water with UV-radiation. It is possible to provide a free space between the irradiation chamber and the outlet chamber. This free space is in the form of a calming zone for the flowing waste water in order to prevent the back-up of water from extending back into the irradiation chamber. However, such a calming zone increases the overall dimensions of the device even more, so that the costs of such a device are further increased again.

SUMMARY OF THE INVENTION

It is an object of the present invention to provide a device for treating liquids with UV-radiation and in particular for treating prepurified waste water. This device can be constructed at substantially more favorable costs and in a more space-saving manner while maintaining optimal disinfection and treatment of liquids. It is of no significance in this connection whether the irradiation chamber is in the form of a chamber closed on all sides, or in the form of a chamber structured in the known manner with an upwardly open channel with a bottom and two side walls.

This object is achieved in accordance with the invention by providing a device for treating prepurified waste water liquid with UV-radiation comprising an irradiation chamber through which the liquid flows; UV-radiation sources positioned in said chamber; an outlet chamber following the irradiation chamber in a downstream direction of flow and provided for draining off the liquid, said outlet chamber being an upwardly open channel with a lower channel bottom and two attached side walls, and having at least one weir element; said weir element having a damming wall with upper overflow edges over which a dammed up liquid overflows and drains off, said damming wall slowing down the flow of the liquid and forming a rear termination of the outlet chamber; the damming wall extends in the direction of flow as an upwardly raised extension of the channel bottom in a slanted manner from a front end to a rear end of the outlet chamber at a flat angle of smaller than 60° relative to channel bottom; several individual weir elements are arranged on the slanted damming wall, said weir elements being separated from each other; said weir elements are formed by upwardly extending tubes, said tubes being open at both ends and having top ends forming overflow edges; and the damming wall is provided in the locations where the tubes are secured on the damming wall with openings corresponding to cross sections of the tubes for draining off the liquid flowing over the overflow edges of the tubes.

According to the invention, the damming wall or termination wall impacted by the flowing waste water extends in the form of a raised extension on the bottom of the channel. This extension rises in a slanted manner from the front end to the rear end of the outlet chamber at a flat angle of less than 60° relative to the bottom of the channel. Thus the flowing waste water no longer impacts a vertical damming wall. The waste water is thereby only gradually slowed down by the slanted damming wall, so that the water flow rate changes only slightly. This means that no backup, or only a minor backup, of the liquid will occur. Thus the even flow of the liquid desired in the irradiation chamber is not influenced, or is only influenced in an insignificant way. A calming zone between the irradiation chamber and the outlet chamber thus can be omitted in connection with the invention. This permits a reduction in the cost of the device as defined by the invention. Furthermore, the overall space requirements of the device of the invention can be reduced as well.

Furthermore, with the device of the invention, several individual weir elements, which are separated from each other, are arranged on the slanted damming wall. Each weir element is formed by an upwardly extending hollow tube, which is open at both ends. The upper ends of the tubes form the overflow edges for the overflow and for draining off the waste water. In the locations where the tubes are secured on the damming wall, the wall is provided with openings corresponding with the cross sections of the tubes for draining off the waste water flowing over the overflow edges of the tubes.

At its top end, each tube has overflow edges, which are predetermined by the circumference of the tube. Since provision is made for a multitude of tubes, a large overall length of the overflow edges is available to the liquid. Thus the device can operate in a satisfactory manner with relatively minor variations in the water level even when waste water is collected in large quantities. Furthermore, the dimensions of the outlet chamber in the longitudinal direction can be kept to a minimum. Due to the slanted damming wall, the flow of the waste water is slowed down only gradually. Thus the waste water can rise in a calmed manner without developing any back-up. Furthermore, when waste water is collected in increased quantities, the additionally dammed up quantity of waste water can flow off without problems over the overflow edges formed by the multitude of tubes. At the same time, the flow in the irradiation chamber is maintained at the desired steady state flow rate. This will assure that the treatment of the waste water with UV-radiation is in an optimal manner.

According to a further embodiment of the invention, the slanted damming wall extends upwardly at a flat angle of between 10° and 50° from the bottom of the open channel. It was found in practical tests that an efficient mode of operation of the device of the invention is assured in these regions.

In another embodiment of the invention, the slanted damming wall is pivotable within the range of the angle between 10° and 50° and adjustable to angle values desired in between these limits. This embodiment permits adaptation of the device to varying amounts of waste water to be expected during the operation.

In a further embodiment of the invention, the outer upper end of the slanted damming wall extends at least up to the vertical level of the upper ends of the tubes. The outer top end of the damming wall forms in this connection another overflow edge for the liquid. Furthermore, it is advantageous that provision is made at the outer top end of the slanted damming wall for an end piece which is vertically adjustable. Thus the overflow edge formed by the end piece is adjustable to a vertical level above the overflow edges of the individual tubes. Adjustments and also readjustments can be made in this way in a simple manner when the device is started up.

According to another embodiment of the invention, the tubes are arranged in a plurality of rows one after the other viewed in the direction of flow of the liquid, whereby the tubes disposed next to one another are arranged displaced inclined relative to each other.

The upwardly extending tubes form with their tube walls a type of damming wall for the flowing liquid. However, the effect of such a damming wall is limited due to the fact that the tubes are round in shape. The displaced arrangement of these tubes assures that the backup of the flowing liquid caused by the tubes is kept within limits to such an extent that such backup will have no adverse effect on the desired steady state flow rate of the liquid in the irradiation chamber.

BRIEF DESCRIPTION OF THE DRAWINGS

Other objects and features of the present invention will become apparent from the following detailed description considered in connection with the accompanying drawings which discloses a few embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
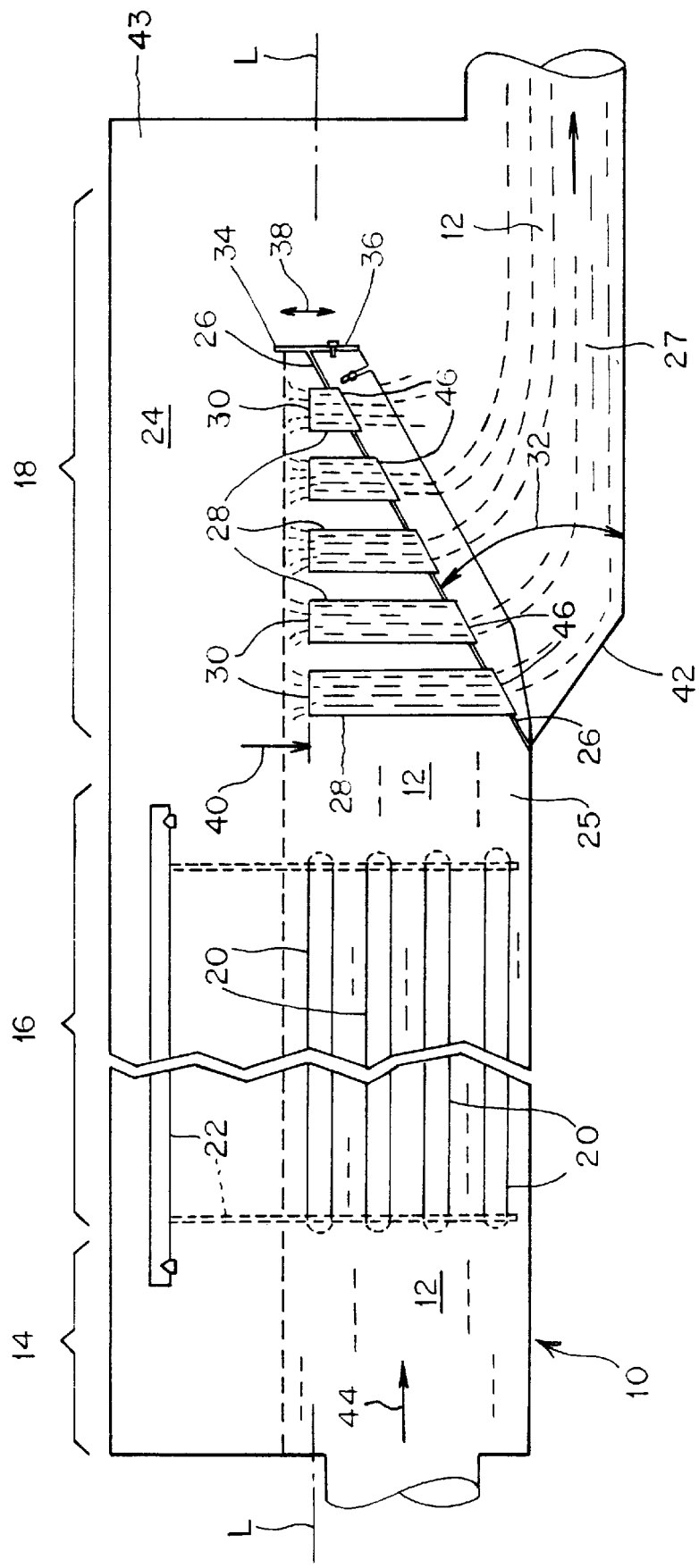
FIG. 1 is a schematic side view of a device for treating liquids with UV-radiation, with an outlet chamber.

Turning now in detail to the drawings, FIG. 1 shows a device 10 according to the invention for treating prepurified waste water with UV-radiation, such waste water coming from a sewage clarification plant not shown. Device 10 is constructed in the form of a channel or gutter 24, which is open at the top and which has a channel or gutter bottom 42 and two side walls 43 extending vertically upward from this bottom 42.

Device 10 comprises an inlet chamber 14, through which waste water 12 is fed to the device 10, and which is followed downstream by an irradiation chamber 16. This irradiation chamber 16 is followed downstream by an outlet chamber 18, from which waste water 12 is drained and admitted to the natural water circulation.

UV-radiation sources 20 arranged next to each other and one above the other with spacings in between are disposed in irradiation chamber 16. These radiation sources extend in the flow direction 44 of waste water 12. UV-radiation sources 20 are arranged in a frame rack 22, so that the UV-radiation sources can be placed in the open channel 24 from the top. UV-radiation sources 20 can also be positioned perpendicular to flow direction 44 of the waste water, and perpendicular to the longitudinal axis L.

In outlet chamber 18, a damming wall 26 extends slanted at a flat angle 32. This damming wall practically forms at the head of outlet chamber 18 an upwardly slanted, raised extension of the channel bottom 42. The angle 32 can be changed by using screw threaded adjustment means 50. Wall 26 extends upwardly from chamber front end 25 to chamber rear end 27 at angle 32.

Figure 2:
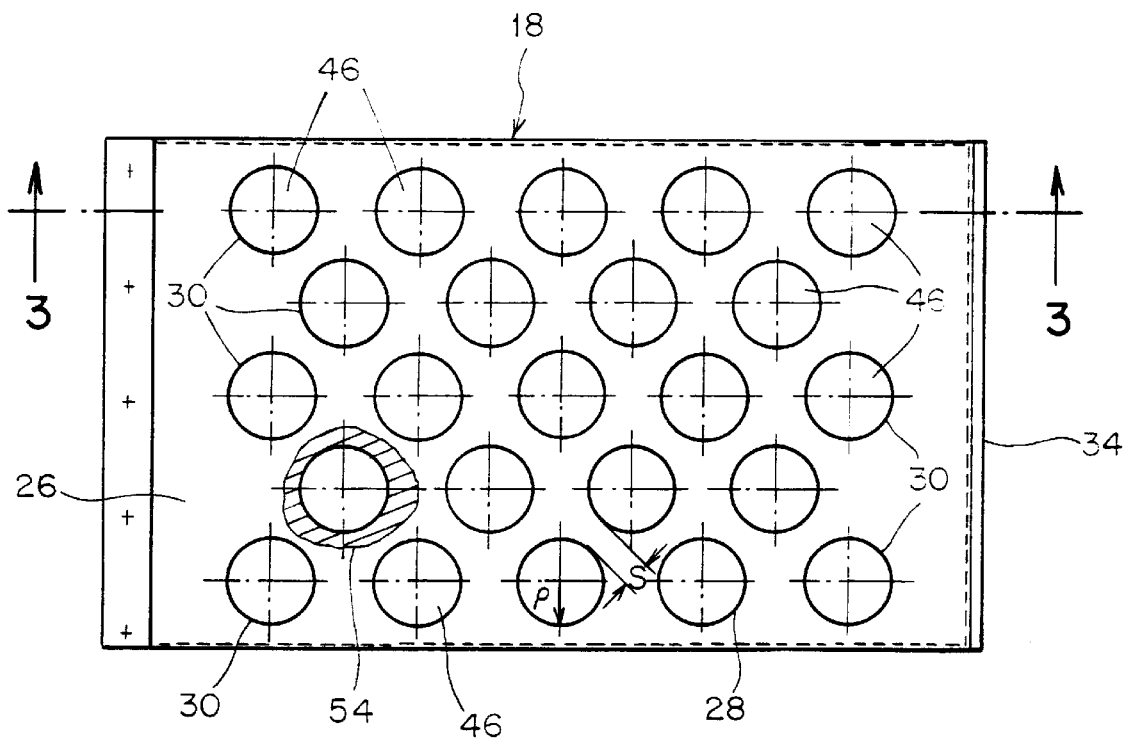
FIG. 2 is a top view of the outlet chamber according to FIG. 1.
Figure 3:
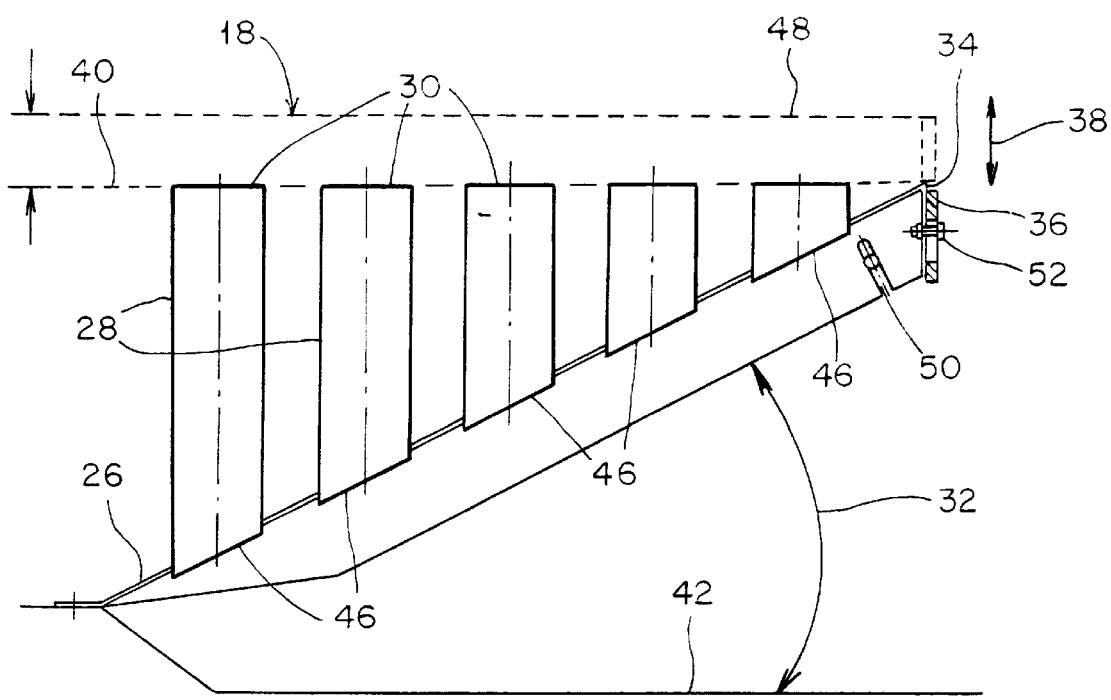
FIG. 3 is a section view of the region of the outlet chamber along line 3—3 of FIG. 2.

The top view according to FIG. 2 and the section view according to FIG. 3 show that vertically arranged tubes 28 are present on the slanted damming wall 26. Each of these tubes is open at both of its ends. The top ends of tubes 28 form overflow edges for waste water 12. In the locations where the tubes 28 are secured on the damming wall 26, the slanted damming wall 26 is provided with openings 46 corresponding to the cross sections of the tubes. The waste water 12 flowing over the overflow edges 30 of tubes 28 thus can flow off through the lower openings of the tubes or through the lower openings 46 of the slanted damming wall 26. The waste water can then be admitted to the discharge system or the natural water circulation.

Therefore, in the device according to the invention, a damming wall extending perpendicular to flow direction 44 of waste water 12 is omitted. Damming wall 26 rather extends slanted, rising slightly at a flat angle, so that the waste water received in outlet chamber 18 is not slowed down abruptly and suddenly, but gradually. This prevents backup of waste water 12, so that the flow profile in irradiation chamber 16 is not influenced in any undesired way, or influenced only to an unnoticeable degree.

Device 10 operates in a satisfactory manner even when waste water 12 is collected in larger quantities because the multitude of tubes 28 assures that even large quantities of waste water 12 can flow off from irradiation chamber 16 unobstructed and without major variations in the water level.

The outer top end of slanted damming wall 26 extending over the total width of gutter or channel 24 reaches at least up to the vertical level 40 of the upper ends of tubes 28. FIGS. 1 and 3 show that an end piece 36 is arranged on the outer top end of the slanted damming wall 26. It is indicated by a double arrow 38 that this end piece 36, which is positioned vertically, can be adjusted in the vertical direction relative to flow direction 44. The top side of end piece 36 forms a further overflow edge 34 for waste water 12. By adjusting end piece 36 in the vertical direction using screw threaded adjustment means 52, it is possible to influence the level of waste water 12 in outlet chamber 18. It is shown in FIG. 3 that the level can be adjusted upwardly to a level 48.

In the embodiments according to FIGS. 1 to 3, the tubes 28 are arranged perpendicular to flow direction 44 and perpendicular to the longitudinal axis L. However, it is possible also within the framework of the invention to arrange the tubes in positions deviating from the vertical direction without influencing by such deviation the mode of operation of the device 10 as defined by the invention. In any case, however, it is advantageous if the overflow edges 30 of tubes 28 extend parallel with channel bottom 42.

Figure 4:
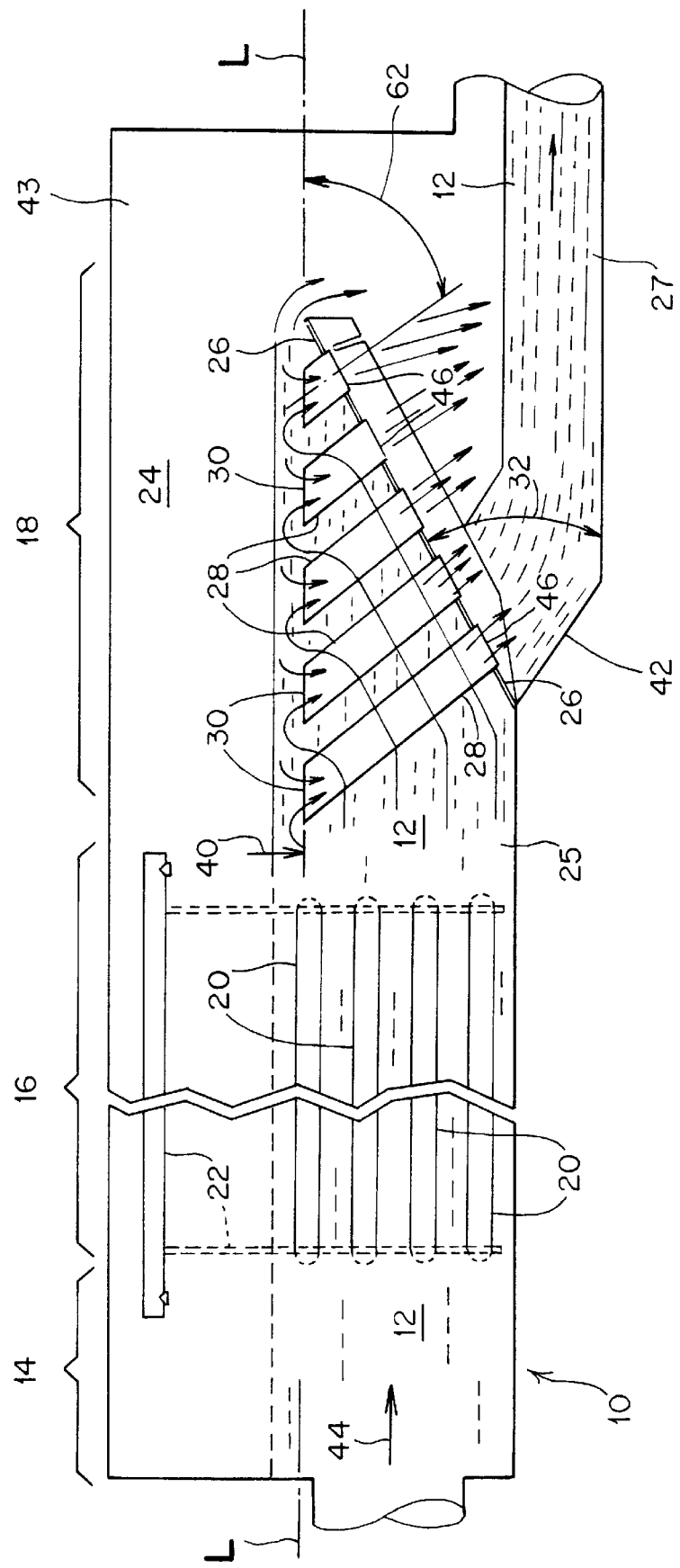
FIG. 4 is a schematic side view of another embodiment of the device of the invention with tubes arranged obliquely.

In another embodiment of the invention, shown in FIG. 4, the tubes 28 are positioned obliquely to the longitudinal axis L, and are slanted relative to the direction of flow 44 through angle 62. Angle 62 is the angle between the center line 60 of the tube 28 and the longitudinal axis L. Angle 62 can range from 30° to 60°, and preferably from 40° to 50°.

Tubes 28 have a round cross section. However, it is possible also to provide the tubes with a different shape, for example with an elliptical cross section.

For obtaining an optimal mode of operation of the device 10 as defined by the invention, it is useful if the tubes 28 are shaped the same, with the exception, of course, of their length. This length varies on account of inclined damming wall 26, so that the overflow edges 30 are located at the same level. The smallest spacing S between the tubes 28 relative to one another corresponds to at least half of the inside radius R of the tubes. With such an arrangement, the device according to the invention operates under optimal conditions, wherein S is ½ R.

In a further embodiment of the invention, the top ends of tubes 28 are shaped like funnels 54. The circumference of the tubes is enlarged in this way at the top ends of the funnels, so that the overall available length of overflow edges 30 is increased and more waste water 12 can drain through tubes 28.

Accordingly, while a few embodiments of the present invention have been shown and described, it is to be understood that many changes and modifications may be made thereunto without departing from the spirit and scope of the invention as defined in the appended claims.

What is claimed is:

1. A device (10) for treating prepurified waste water liquid (12) with UV-radiation comprising an irradiation chamber (16) through which the liquid (12) flows;

UV-radiation sources (20) positioned in said chamber (16);

an outlet chamber (18) following the irradiation chamber (16) in a downstream direction of flow (44) and provided for draining off the liquid (12), said outlet chamber being an upwardly open channel (24) with a lower channel bottom (42) and two attached side walls (43), and having at least one weir element;

said weir element having a damming wall (26) with upper overflow edges over which a dammed up liquid (12) overflows and drains off, said damming wall slowing down the flow of the liquid (12) and forming a rear termination of the outlet chamber (18);

the damming wall (26) extends in the direction of flow (44) as an upwardly raised extension of the channel bottom (42) in a slanted manner from a front end (25) to a rear end (27) of the outlet chamber (18) at a flat angle of smaller than 60° relative to channel bottom (42);

several individual weir elements are arranged on the slanted damming wall (26), said weir elements being separated from each other; said weir elements are formed by upwardly extending tubes (28), said tubes being open at both ends and having top ends forming overflow edges (30); and the damming wall (26) is provided in the locations where the tubes (28) are secured on the damming wall (26) with openings (46) corresponding to cross sections of the tubes for draining off the liquid (12) flowing over the overflow edges (30) of the tubes (28).

2. The device according to claim 1, wherein the slanted damming wall (26) extends at a flat angle (32) of between 10° and 50° relative to the channel bottom (42).

3. The device according to claim 2, comprising means (50) for adjustably pivoting the slanted damming wall (26) within the angle range between 10° and 50°.

4. The device according to claim 1, wherein an outer top end of the slanted damming wall (26) extends up to a vertical level (40) of the top ends of the tubes (28) and forms a further overflow edge (34) for the liquid (12).

5. The device according to claim 4, comprising an end piece (36) on the outer top end of the slanted damming wall (26), said end piece having means for vertical adjustability (52) so that the overflow edge (34) formed by the end piece (36) is adjustable to a vertical level both above and below the overflow edges (30) of the individual tubes (28).

6. The device according to claim 1, wherein in the direction of flow (44) of the liquid (12), the tubes (28) are arranged in a number of rows one after the other; and that the rows disposed next to one another are arranged displaced and slanted relative to each other.

7. The device according to claim 6,
wherein the tubes (28) are perpendicular to the direction of flow (44).

8. The device according to claim 6,
wherein the tubes (28) are slanted relative to the direction of flow (44); and the overflow edges (30) of the tubes extend parallel to the channel bottom (42).

9. The device according to claim 1,
wherein each tube (28) has a circular cross section.

10. The device according to claim 1,
wherein the tubes (28) are vertical and have a cross section deviating from a circular shape.

11. The device according to claim 1,
wherein the tubes (28) are identical except for each's length; and that the smallest spacing between the tubes relative to one another corresponds with at least half of an inside radius of the tubes.

12. The device according to claim 1,
wherein the top ends of each of the tubes (28) are disposed at a same vertical level.

13. The device according to claim 1,
wherein the top ends of each of the tubes (28) are disposed at different vertical levels.

14. The device according to claim 1,
wherein the top ends of each of the tubes (28) have the shape of a funnel (54).

* * * * *